United States Patent [19]

Talwar

[11] 4,161,519

[45] Jul. 17, 1979

[54] PROCESS FOR PREPARING AN ANTIPREGNANCY VACCINE

[75] Inventor: Gursaran P. Talwar, New Delhi, India

[73] Assignee: All India Institute of Medical Sciences, New Delhi, India

[21] Appl. No.: 789,455

[22] Filed: Apr. 21, 1977

Related U.S. Application Data

[63] Continuation of Ser. No. 544,677, Jan. 28, 1975, abandoned.

[51] Int. Cl.² .................. A61K 37/38; A61K 39/00
[52] U.S. Cl. ........................................ 424/88; 424/8; 424/12; 424/85; 424/100; 424/177
[58] Field of Search ................ 424/8, 12, 85, 88, 100, 424/177

[56] References Cited

FOREIGN PATENT DOCUMENTS 2421943  11/1974  Fed. Rep. of Germany ............ 424/85

OTHER PUBLICATIONS

Ross, Excerpts Med. Found., 1971, Protein & Polypeptide Hormones, Proc. Int. Symp., 1971, p. 399.
Stevens, Ob. & Gyn. vol. 42, Oct. 1973, pp. 485–495;496–506
Donini, Acta Endocrinal., vol. 73, 1973, pp. 133–145.

*Primary Examiner*—Anna P. Fagelson
*Attorney, Agent, or Firm*—Brumbaugh, Graves, Donohue & Raymond

[57] ABSTRACT

A vaccine comprising a conjugate of an antigenic carrier with beta sub-unit of human chorionic gonadotropin, or derivatives or fragments thereof, purified by procedures which minimize cross-reactivity with LH, such as immunosorption with heterologous LH antiserum prior to conjugation, and a process for making the vaccine. In addition, a process for preventing pregnancy using said vaccine is described.

9 Claims, 10 Drawing Figures

PROCESS FOR PREPARING AN ANTIPREGNANCY VACCINE

This is a continuation application of the copending application, Ser. No. 544,677 filed Jan. 28, 1975, now abandoned.

The present invention relates to a vaccine for preventing pregnancy, to a method of preparing the vaccine and to the method of using the vaccine for preventing pregnancy.

A variety of methods for controlling fertility and for preventing and terminating pregnancy are known. A variety of approaches such as condomes, IUCD's, mechanical devices, spermicidal creams and jellies, foam tablets, oral pills, etc. are currently available as a prevention against pregnancy. These methods, though effective to a variable extent, also have limitations. Most of them require constant motivation on the part of the user. Some require specialized medical attention.

The development of immunological methods of controlling fertility has been the subject of experimentation going back at least to the beginning of this century. A number of approaches are described by Albert Tyler in "Approaches to the Control of Fertility Based on Immunological Phenomena," *Journal of Reproduction and Fertility*, (1961)2, pages 473–506.

Among the approaches followed in recent years by investigators have been immunization with placental, fetal materials, and hormones. To date, however, to Applicant's knowledge, there has been no effective antifertility vaccine developed. The present approach is based upon eliciting antibody response by active immunization to a hormone critical to establishment and maintenance of pregnancy.

It is an object of the present invention to provide an antipregnancy vaccine.

It is a further object of the present invention to provide a process for preventing pregnancy in mammals including humans utilizing vaccines which are free of significant adverse side-reactions.

It is a further object of the present invention to provide a method for preparing an antipregnancy vaccine which produces antibodies with minimal cross-reaction with other endogenous hormones at physiological levels.

It is a further object of the present invention to provide a process which prevents pregnancy using a vaccine that can be administered by paramedical auxiliary personnel and which requires only periodic supplemental treatment.

It has now been found that a vaccine for the prevention of pregnancy is provided by forming a conjugate of a subject-compatible immunogenic carrier with a preparation of beta sub-unit of hCG, the preparation being free to determinants capable of reacting with high affinity with anti LH sera. Specifically, antipregnancy vaccines are obtained with conjugates of said carriers with a substance selected from the group consisting of (i) C-terminal fragments of the beta sub-unit of human chorionic gonadotropin, having from 30 to 38 amino acid residues, (ii) the nitro derivative of the beta sub-unit of hCG, and (iii) the immunochemically purified beta sub-unit of hCG, all substances free of determinants capable of reacting with high affinity with anti LH sera. The term immunochemically purified, in this context, includes treatment which removes components of the beta sub-unit preparation which, if retained, would cause formation of antibodies that would cross-react with endogenous LH. The vaccine of the present invention is substantially free of cross reaction with other endogenous hormones, such as the pituitary hormones required for normal function of reproductive organs.

In accordance with one preferred embodiment of the invention, the beta sub-unit is separated from the alpha sub-unit of human chorionic gonadotropin in accordance with known procedures, is thereafter chemically purified by known means, and then immunochemically purified using a heterologous anti LH immunosorbent. The vaccine in a preferred form is a conjugate of a chemically and immunochemically purified form of beta sub-unit of human chorionic gonadotropin with tetanus toxoid in molecular proportions of about 1:5 to about 1:20. The conjugation takes place in the presence of a condensing agent such as glutaraldehyde or ethyl aminopropyl carbodiimide to obtain a covalently linked conjugate. The conjugate is thereafter subjected to the conventional steps of dialyzing, sterility control and precipitation to form the vaccine.

As known in the art, placenta is a tissue which develops only in pregnancy; it is not a normal part of the nonpregnant female. The vaccine of this invention is capable of counteracting the establishment and maintenance of pregnancy. In humans, for example, a critical hormone, human chorionic gonadotropin is produced by the trophoblasts on about the eighth day after fertilization. This hormone supports, at this stage, the corpus luteum and ensures the receptivity of the uterus. The hormone may also protect the blastocyst by other means. Its neutralization results in the onset of menstruation, thus preventing the maintenance of pregnancy.

Human chorionic gonadotropin (hereinafter sometimes referred to as hCG) is a glyco-proteinic hormone composed of 2 sub-units: alpha and beta. The alpha sub-unit is nearly identical with the respective alpha sub-units of the hormones Thyroid Stimulating Hormone (TSH), Follicle Stimulating Hormone (FSH), and Luteinizing Hormone (LH). The beta sub-unit of the hormone, in each case, ascribes principally the hormonal specificity.

The beta sub-unit of hCG is a polypeptide of 146–147 amino acids with 3 out of 5 carbohydrate residues in the C-terminal end. A portion of the beta sub-unit bears amino acid homologies with the beta sub-unit of LH. The beta hCG prepared by dissociation of highly purified hCG has a fair degree of microheterogeneity. The protein resolves into 8 bands by electrophoresis on analytical polyacrylamide gels. This microheterogeneity is observed in commercially available hCG, which is prepared from pregnancy urine. The microheterogeneity may be due to a variable degree of cleavage and/or modification of the molecule during its passage through various tissues.

hCG as a whole molecule or the beta sub-unit of hCG, when injected into women, does not elicit the formation of antibodies capable of neutralizing the activity of hCG. It can, however, be made antigenic by coupling it with strongly antigenic haptens. Diazotized sulfanilic acid derivatives have been tried and it has been demonstrated that anti hCG antibodies are induced in postmenopausal women. This is described by Vernon C. Stevens and C. Deans Crystle in "Effects of Immunization with Hapten-Coupled HCG on the Human Menstrual Cycle", *Obstetrics and Gynecology*, Vol. 42, No. 4, October, 1973. However, subjects had a depression or obliteration of mid-cycle LH peaks, suggesting to the investigator that the antibodies cross-reacted in vivo with endogenous LH. Such a cross-reaction with a pituitary hormone required for normal function of reproductive organs is undesirable and potentially hazardous.

It is important according to the present invention that the beta sub-unit of hCG used in the reaction mixture be highly purified both chemically and immunochemically. The chemical purification of the beta sub-unit may be effected in any manner known in the art, such as the procedure described in Morgan, F. J. and R. E. Canfield, *Endocrinology* 88, 1045, 1971; and F. J. Morgan, R. E. Canfield, J. L. Vaitukaitis, and G. T. Ross, *Endocrinology* 94, pages 1601–1605, 1974. Another suitable method of obtaining a chemically pure beta sub-unit of hCG is described by Swaminathan, N. and Bahl, O. P. in "Dissociation and Recombination of Subunits of Human Chorionic Gonadotropin", *Biochem. Biophys. Res. Commun.*, Vol. 40, page 422, (1970). However, these chemical purification procedures are not sufficient to remove determinants capable of reacting with high affinity with anti LH sera.

The immunochemical purification step consists of dissolving the chemically purified beta sub-unit of human chorionic gonadotropin in a physiological solvent, such as phosphate buffered saline, and stirring the solution at room temperature for a controlled length of time with an immunosorbent, such as rabbit antiovine LH. The treatment with a heterologous anti LH immunosorbent, under carefully controlled conditions, is designed to remove those parts of the preparation which have determinants capable of reacting with high affinity with anti LH sera. The immunosorbent used in the process of this invention may be selected from any of several heterologous LH antisera such as rabbit antiovine LH, monkey antiovine or anti bovine LH. The stirring is effected at a temperature of, for example, 25° C., for periods of from 1 to 60 minutes or more, depending upon the temperature, the nature of the particular batch of beta sub-unit of hCG and the potency of immunosorbent used. The optimum condition should be determined for each sample of beta sub-unit preparation and for each immunosorbent. The preparation is thereafter subjected to the step of centrifugation; the precipitate is discarded and the filtrate contains chemically and immunochemically purified beta sub-unit of human chorionic gonadotropin.

The C-terminal fragments of the beta sub-unit may be prepared by enzyme cleavage of beta sub-units of hCG or by synthesis of the C-terminal peptides by the standard procedures of Merrifield, R. B., *Journal of Am. Chem. Soc.*, Vol. 86, 304, 1964. Suitable methods utilizing enzyme cleavage are described in Bahl et al., *Biochem. Biophys. Res. Commun.* 48, 416, 1972, and Morgan et al., *Mol. Cell. Biochem.* 2, 97, 1973.

The nitro derivative of beta sub-unit of hCG may be prepared by the process described in Sokolousky et al., Biochemistry 5, pages 3582–3589 (1966).

These preparations are subjected to the immunochemical purification step to exclude determinants capable of reacting with high affinity with anti LH sera.

The term "high affinity" as used according to this invention describes a characteristic of these moieties which combine with the anti LH sera at a rapid rate at the temperature used. The anti LH sera for this purpose is preferably raised to heterologous LH.

The preparation of beta sub-unit of human chorionic gonadotropin free of determinants capable of reacting with high affinity with anti LH sera is then reacted with a subject-compatible, immunogenic carrier such a tetanus toxoid in desired proportions using a condensing agent, thus conjugating the beta sub-unit with the carrier. Suitable carriers for use in preparing the vaccine of the present invention include tetanus toxoid, polymerized flagellin, KLH (Keyhole Lympet Hemocyanin), dextran, heat or irradiation inactivated polio and yellow fever viruses, heat or irradiation inactivated typhoid and paratyphoid vaccines, cholera toxoid, Bacillus of Calmette and Guerin, antiplasmodium vaccine, pertussis and diphtheria toxoid and biodegradable polymers, such as polylactic acid, polyglycolic acid, collagen, synthetic polypeptides, and polynucleotides.

In accordance with one of the preferred embodiments of the present invention, the reaction product is a complex polymer of tetanus toxoid and the chemically and immunochemically purified beta sub-unit of human chorionic gonadotropin conjugated covalently in the molecular proportions from about 1:5 to about 1:20 in the presence of a condensing or coupling agent such as glutaraldehyde or 1-ethyl-3-(3-dimethyl aminopropyl) carbodiimide.

When the condensing agent consists of 1-ethyl-3-(3-dimethyl-aminopropyl) carbodimide, purified tetanus toxoid and beta sub-unit of human chorionic gonadotropin is admixed in molecular proportions within the range given above together with the condensing agent and the mixture is then incubated at a temperature not exceeding 25° C., and for a period not exceeding six hours depending upon the temperature. It is preferred that the reaction is carried out at a temperature not exceeding 10° C. and for a period of 4 to 6 hours.

When the condensing agent consists of glutaraldehyde, purified tetanus toxoid and beta sub-unit of human chorionic gonadotropin is admixed in the desired molecular proportions together with the condensing agent and the mixture is then incubated at a temperature not exceeding 37° C. and for a period not greater than six hours. Preferably, the step of incubation is carried out at a temperature of about 20° to about 30° C. and for a period of 2 to 4 hours.

In the embodiment using the C-terminal fragments of B-hCG, it is combined with the tetanus toxoid in the molecular proportions of toxoid to fragments ranging from 1:10 to 1:100, preferably 1:40. When the nitro derivative is used in the conjugate, it is used in the molecular proportion, toxoid to derivative, of about 1:5 to about 1:20.

The compound so obtained is thereafter dialyzed thoroughly against phosphate buffer saline pH 7.2, 0.005 M in cold, e.g. 5° C., and collected in a sterile tube using a millipore filter and syringe assembly, using saline for transfer. The preparation is then subjected to the step of sterility testing, in a manner known as such in the art, to ensure the absence of micro-organisms.

Subsequent to the step of sterilization, the preparation is precipitated on alumina, using sterile potash alum $Alk(SO_4)_2.12H_2O$ and sterile sodium carbonate solutions. Instead of potash alum any other suitable adjuvants may also be used. However, it has been found that precipitation on alumina protects the active substance from adsorption on glass containers and also provides a long lasting response. The vaccine is preferably used as an emulsion with vegetable oils at the time of injection, and this further improves antigenicity.

Further objects and advantages of this invention will be more apparent from the ensuing description relating to Examples for the preparation and use of the vaccine.

EXAMPLE I

An antipregnancy vaccine was prepared by the following procedure:

A. Chemical Purification of Beta sub-unit of human Chorionic Gonadotropin

Purified human chorionic gonadotropin was prepared from crude hCG by the method of Canfield et al.* It was incubated at 40° C. for 1 hour with 8 M freshly prepared urea solution that had been purified on a mixed cation-anion exchange resin column, specifically a bed of equal quantities of Dowex-1 X-8 and Dowex-50 X-4, 200 mesh. The column size was 2 × 40 cm. In the presence of urea, the beta sub-units are dissociated and then separated by the method described by Morgan and Canfield, *Endocrinology* 88, 1045, 1971. In accordance with this process, the mixture is passed through ion exchange columns and Sephadex columns repeatedly to obtain the dissociated beta sub-unit with minimal contamination of the whole human chorionic gonadotropin molecule, or its alpha sub-unit.

*Canfield et al. Recent Progr. Horm. Res. 27: 124, 1971

B. Immunochemical purification of beta sub-unit of human chorionic gonadotropin From the beta sub-unit of hCG prepared in step A. above, micro samples were taken. A series of 100 ug samples, 5 in number, of the beta sub-unit of hCG were each dissolved in 0.1 ml of 100 mM sodium phosphate ($NaH_2PO_4$ and $Na_2HPO_4$) buffered saline (0.85% NaCl) (PBS) (pH 7.2). Each sample was stirred at room temperature (25° C.) with an immunosorbent of rabbit anti-ovine LH prepared in the manner described in C. infra. Stirring times varied from 1, 5, 10, 20 and 30 minutes. After the mixing, the tubes were centrifuged for 10 minutes at 0°–4° C. The supernatent from each tube was tested for reactivity against anti hCG and anti LH. By this test the appropriate conditions for purifying the entire batch of beta sub-unit of hCG prepared in A. were determined to be 30 minutes of stirring at 25° C. The selection of 30 minutes was based on the observation that the sample provided a supernatent with minimum level of reactivity with LH.

Figure 1:
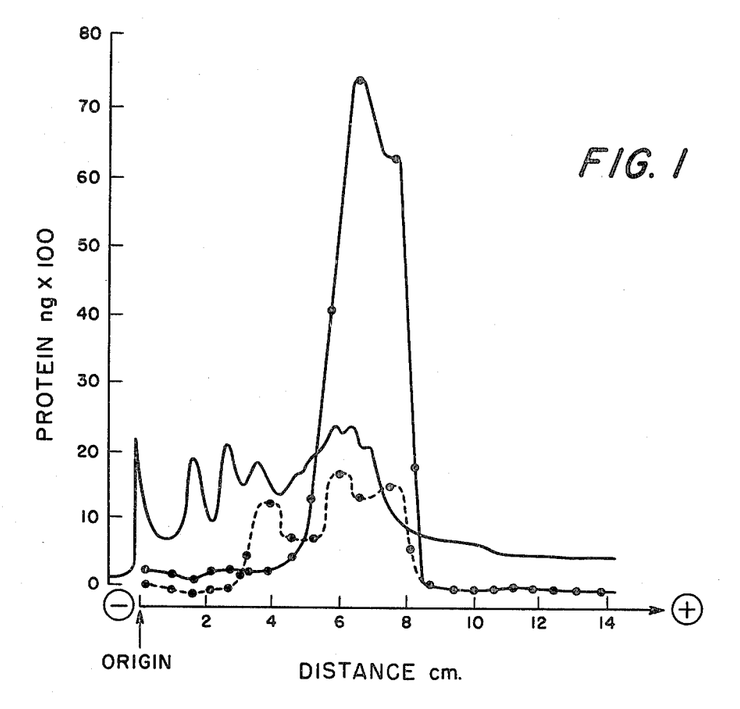
Figure 2:
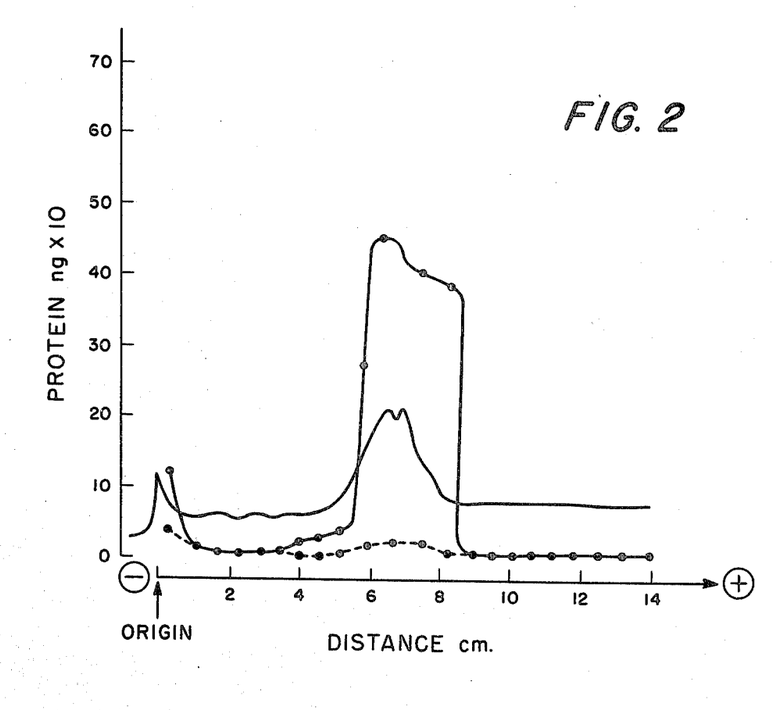

The characteristics of the beta hCG of the purified beta sub-unit of hCG prepared in A. above was compared with the immunochemically purified beta sub-unit preparation prepared above in B. FIGS. 1 and 2 of the attached drawings show the reactivity of the respective preparations with anti hCG and anti LH serum before (FIG. 1) and after (FIG. 2) the immunosorption purification step. The absorption step also improves the microheterogeneity of the preparation. Referring to FIGS. 1 and 2, the beta hCG preparations were subjected to electrophoresis in 7.5% analytical polyacrylamide gels at pH 9.0. A set of the gel was stained for densimetric measurements and another identical gel was transversely sliced into about 2.5 mm thick segments. Proteins from each segment were eluted in 0.9% sodium chloride solution. In each of FIGS. 1 and 2, the curve (________) represents proteins measured by densitometry; the curve (●——●) represents proteins competing with beta $hCG^{125}I$ for binding with anti beta hCG serum; and the curve ●-----● represents proteins competing with $hLH$ $^{125}I$ for binding with anti hLH serum. It will be noted that the immunochemically purified preparation shows a substantial reduction in reactivity with anti hLH serum.

It may be noted that the optimum conditions of time of stirring and temperature are determined by the nature of the particular batch of beta sub-unit and the potency of the immunosorbent used. It is recognized that the latter varies with the titres of the antiserum used and with storage period of the immunosorbent.

C. Preparation of Immunosorbent 10 ml of antiserum (rabbit antiovine LH) obtained by immunization of rabbit with ovine LH is dialyzed thoroughly against PBS at 0°–4° C. and pH is adjusted to pH 5 with 1 M sodium acetate buffer. 3 ml of a 2.5% aqueous solution of glutaraldehyde is added gently with stirring. The reaction mixture is allowed to stand at room temperature (25°) for 3 hours. The polymerized material is homogenized in a Potter ElveJhem homogenizer with Teflon pestle. It is washed with PBS repeatedly till free of 280 mµ absorbing material (non-polymerized free protein). It is then washed with 200 mM glycine - HCl buffer pH2.2 and neutralized with 2 M $K_2HPO_4$ solution and finally equilibrated with PBS. The immunosorbent is stored at 4° C. with 0.1% Na azide as a preservative in glycine HCl buffer pending the follow-up.

$D_1$ Preparation of Vaccine Using 1-Ethyl-3-(3-Dimethylaminopropyl) Carbodiimide as Condensing Agent

Preparation (for 40 doses)

3.2 mg beta sub-unit of hCG, as prepared in B. above was mixed with 400 LF tetanus toxoid (1500 Lf/mg protein N) and 16 mg of 1-ethyl-3-(3-dimethyl-aminopropyl) carbodiimide in 6.5 ml of PBS, and the solution was incubated at 10° C. for 5 hours with occasional shaking. The molecular proportion of tetanus toxoid to β-sub-unit of hCG is about 1:10. The reaction product was dialyzed thoroughly against phosphate buffer saline pH 7.2, 0.005 M in cold. The product was collected in a sterile tube using a millipore filter and syringe assembly, and using saline for transfer. The product was tested for sterility on thioglycolate medium for seven days. It was then adsorbed on potash alum. $Alk(SO_4)_2.12H_2O$ using sterile 10% potash alum and sterile 10% sodium carbonate solutions. The vaccine was then distributed, sealed into ampules, and sampled for pyrogens and sterility.

$D_2$ Preparation of Vaccine Using Glutaraldehyde as Condensing Agent — Preparation of 1 Dose 80 ug of the beta sub-unit of hCG, as prepared in B. above was mixed with 1 dose tetanus toxoid, 10 Lf units and 50 ul of 1% aqueous glutaraldehyde. The mixture was incubated at 30° C. with occasional mixing for 3 hours, and then dialyzed thoroughly against PBS pH 7.2, 0.005 M. The rest of the procedure is the same as that described in preparation $D_1$.

Properties

The vaccine prepared in accordance with $D_1$ described above, hereinafter designated Beta-hCG-TT was found to be immunogenic in mice, rabbits, goats, monkeys, as well as in the human female. The vaccine under $D_2$ described above was found to have similar immunogenic characteristics in monkeys. Both gave rise to a fairly long lasting antibody response.

Figure 3:
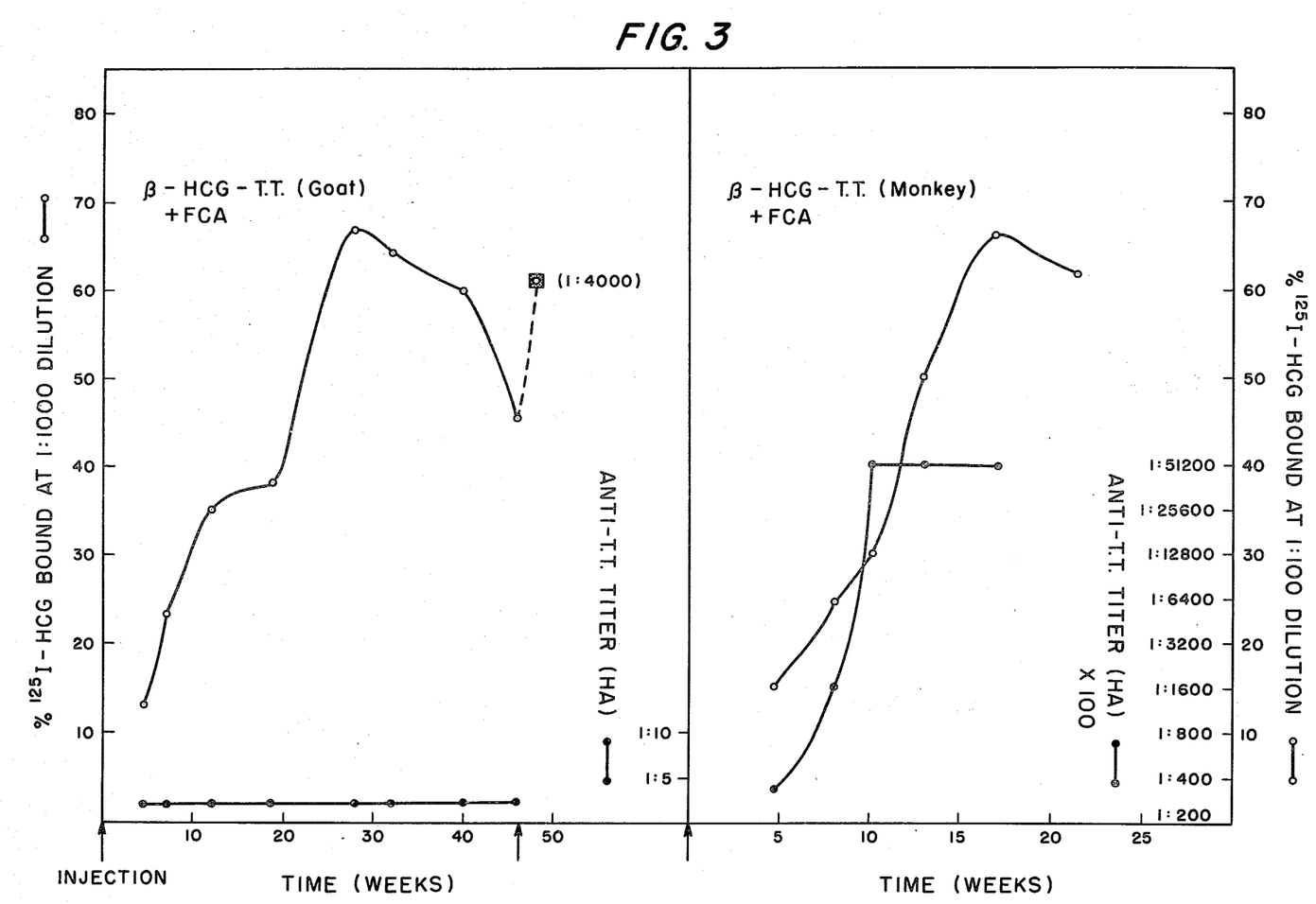

A single injection of the vaccine $D_1$ given with Freund's adjuvant at multiple sites in the goat induced rising antibody titers for about 9 months after which a plateau is reached. This was followed by a declining trend. A second booster injection in the declining phase lead to a sharp rise in antibody titers. This is shown in FIG. 3.

The pattern of response in 10 experimental rhesus monkeys is found to be similar, although there are individual variations. This is also shown in FIG. 3.

In examining the immunological properties of anti (Beta-hCG-TT) serum, it was found that such serum raised in the goat or monkey reacts immnologically with whole hCG molecules. The antiserum does not give a cross-reaction with human growth hormone (hGH), human prolactin, and human placental lactogen (hPL), FSH, TSH, or LH, as tested at the physiological and surge levels. Table 1 below summarizes the results.

species, namely, the rodents and the monkey. Its tolerance has also been tested in 65 mice, 7 rabbits, and 13 monkeys for periods ranging up to 1 year and beyond. The survival of the immunized animals was 100%. Other parameters such as hematology (hemoglobin, TLC/DLC, PVC, peripheral smear examination for platelets, reticulocytes) hepatic functions (serum bilirubin, alkaline phosphatase, the transaminases GOT and GPT, LDH isoenzymes, cholinesterase), Renal function tests, blood glucose, serum lipids, cholesterol, triglyceides, free fatty acids, and thyroid function tests were normal in immunized monkeys. The immunized monkeys did not develop immediate (Arthus) or delayed hypersensitivity to hCG.

Clinical Studies

Six human female volunteers in the reproductive age group of 20–32 years were injected with either the vaccine preparation made according to $D_1$ above, or

TABLE I
SPECIFICITY OF ANTI B HCG-T.T. SERA FROM MONKEY AND GOAT

| Hormone | Concentration | % BOUND to Antibody | | % Completion | | Maximum conc. where competition appears. |
|---|---|---|---|---|---|---|
| | | Monkey (1-5000) | Goat (1:4000) | Monkey | Goat | |
| B-HCG | 10 ng | 13 | 9 | 87 | 91 | — |
| | 2 ng | 72 | 68 | 2 | 32 | — |
| HCG | 10 ng | 30 | 30 | 70 | 70 | — |
| | 2 ng | 70 | 85 | 30 | 15 | — |
| HLH | 1.2 ng** | 100 | 96 | 0 | 4 | 5 ng |
| | 0.4 ng* | 100 | 98 | 0 | 2 | — |
| HFSH | 0.7 ng** | 100 | 100 | 0 | 0 | 50 ng |
| | 0.3 ng* | 100 | 100 | 0 | 0 | —ng |
| | 0.3 ng* | 100 | 100 | 0 | 0 | — |
| HTSH | 2.5 ng** | 100 | 100 | 0 | 0 | >>100 ng |
| HPL | 12.5 ng** | 100 | 100 | 0 | 0 | >>1 ug |
| HGH | 0.25 ng** | 100 | 100 | 0 | 0 | >>1 ug |

*Basic or tonic concentration
**Maximum physiological concentration

Figure 4:
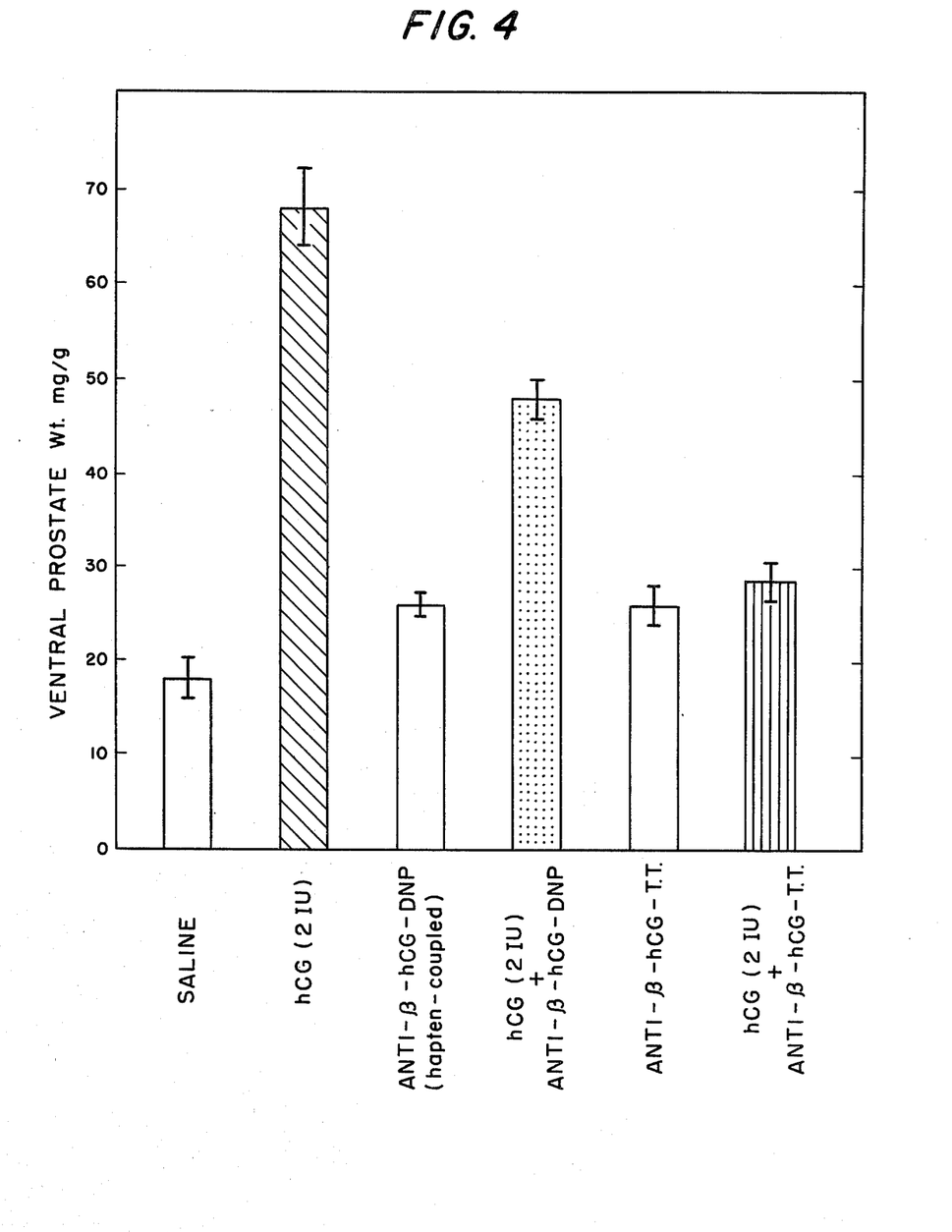

The biological properties of the anti (Beta-hCG-TT) serum produced in the goat and monkey and the ability of the serum to neutralize hCG was tested in a number of systems. It was found effective for inhibition of the hCG induced increase of the ventral prostate weight in immature rats. Experimental data summarizing this work is shown in FIG. 4. It also counteracted the hCG induced rise in production of progesterone in corpus luteum slices in vitro. This is shown in Table II.

TABLE II

| EFFECT OF ANTI β-HCG-TT ON PROGESTERONE SYNTHESIS BY CORPUS LUTEUM | |
|---|---|
| Additions | P. ug/g tissue* |
| 1. None | 79.4 ± 15.2 |
| 2. + HCG (0.1 ug/ml) | 183.2 ± 30.6 |
| 3. + HCG + anti β-TT | 105.4 ± 23.4 |
| 4. + anti β-TT | 96.7 ± 23.2 |

*Mean ± S.E. of 6 experiments

Figure 5:
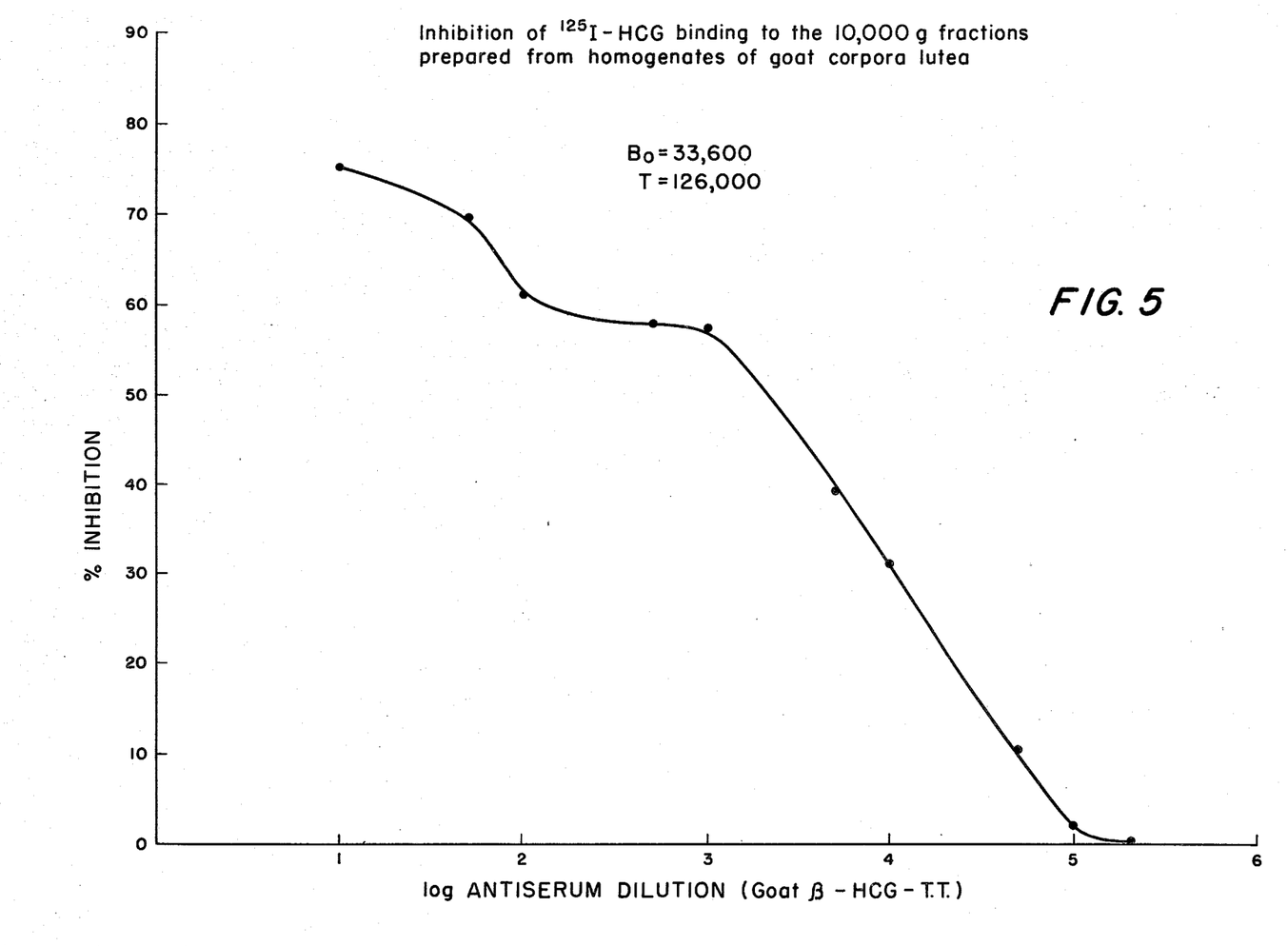

It also prevents the binding of hCG to receptors in membrane preparations from the testes and ovaries. Experimental data showing this is summarized in FIG. 5. All these tests show that the antibodies raised against the compound Beta-hCG-TT has the ability to not only react immunologically with the whole hCG molecules but also to neutralize its biological activity.

The (Beta-hCG-TT) vaccine preparation $D_1$ was tested for safety as per British Pharmacopoeia requirements, and was found to give rise to no death in guinea pigs over the 4 weeks of observation period. It was also devoid of acute and subacute toxicity as tested in two with alternate placebos in blind trials. Since the object of these tests was to establish the immunogeneity of the vaccine of the present invention, the six women selected for this stage of the testing were those which had previously undergone tubal ligation. The placebos, in all cases, gave no response. Each of the three subjects receiving the vaccine elicited antibody response against both tetanus toxoid and human chorionic gonadotropin. Following a lag period which lasted from 4–6 weeks from subject to subject, a progressive rise in antibody titers followed. Antibodies were also elicited simultaneously to tetanus.

Figure 6:
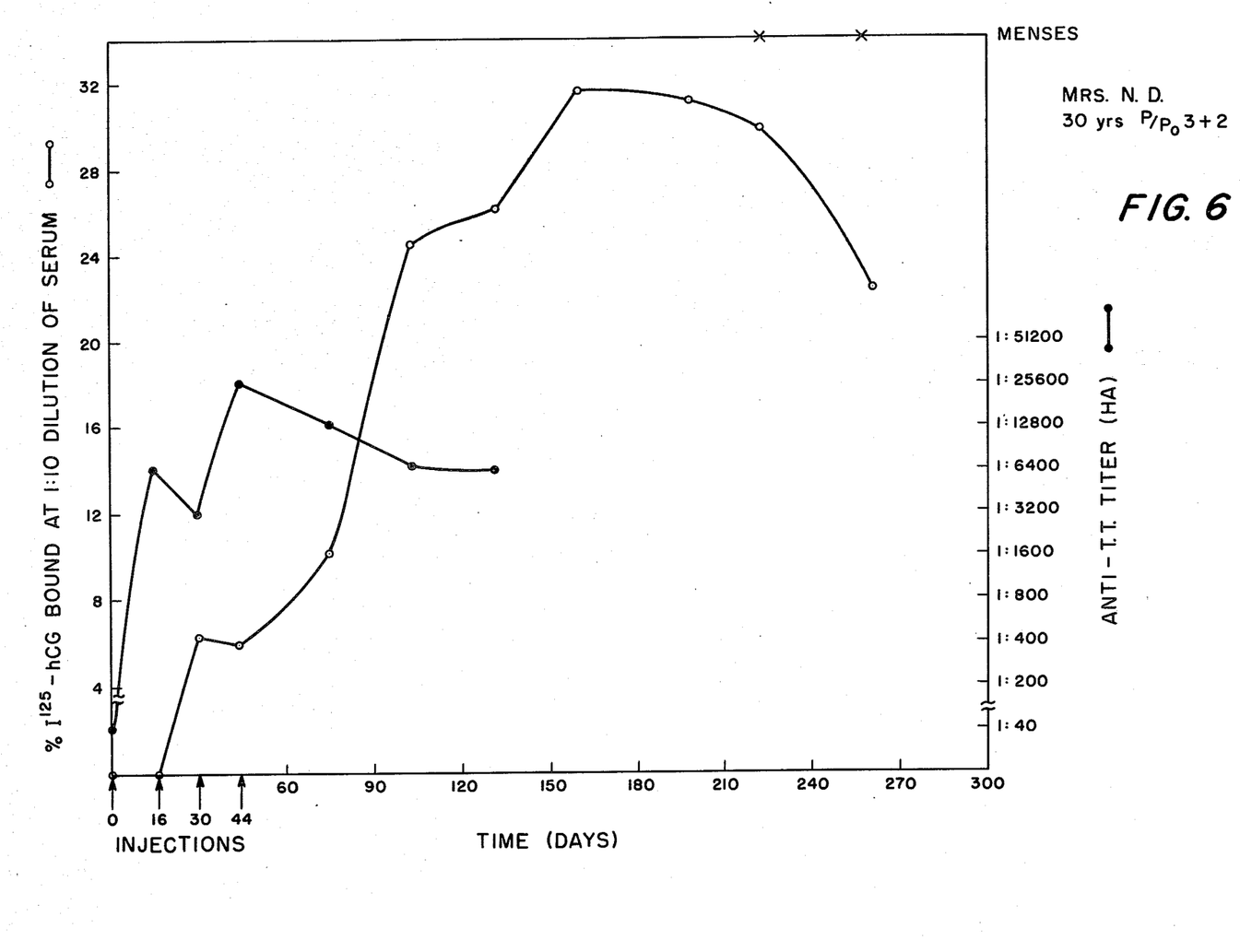
Figure 7:
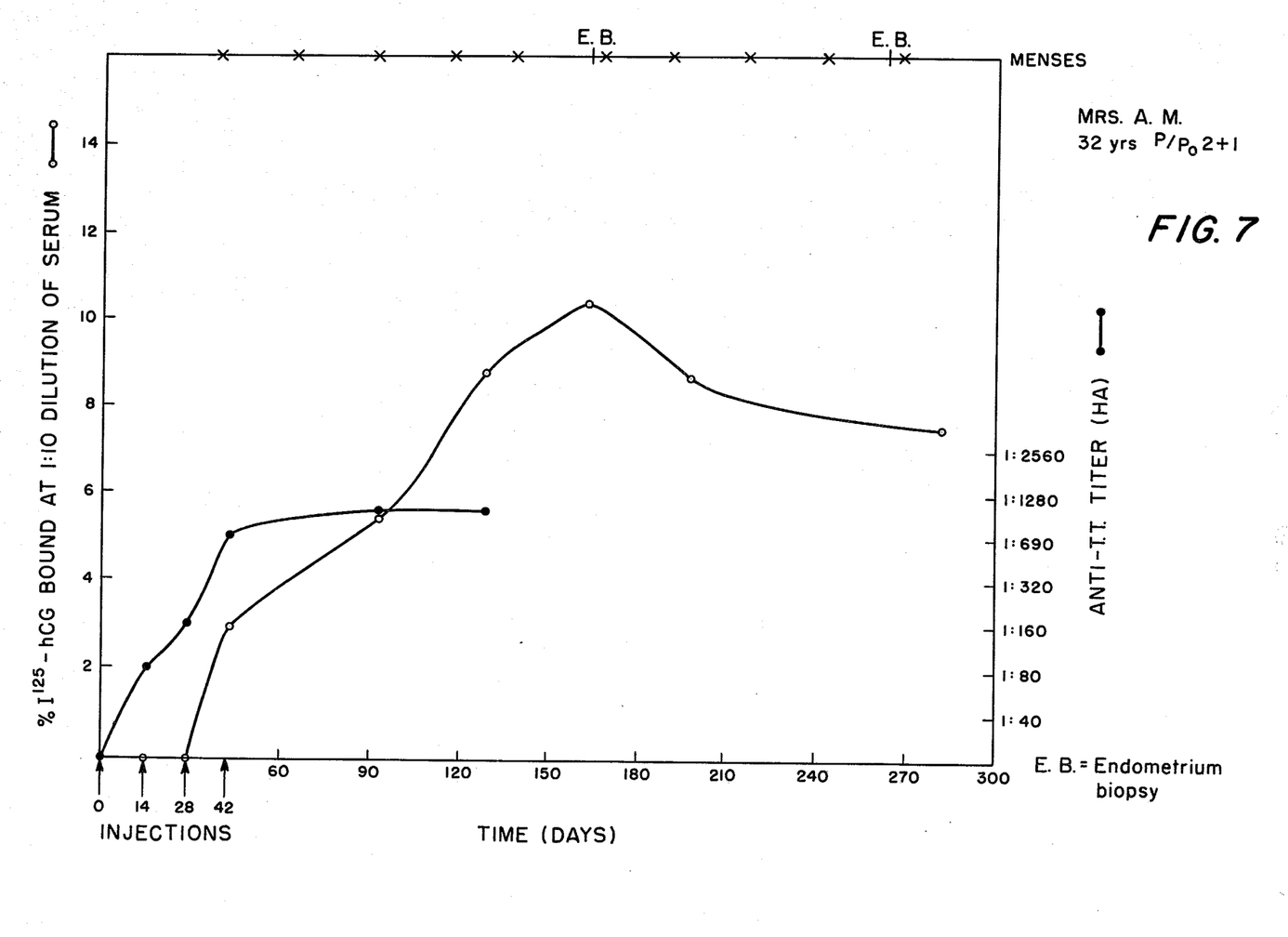
Figure 8:
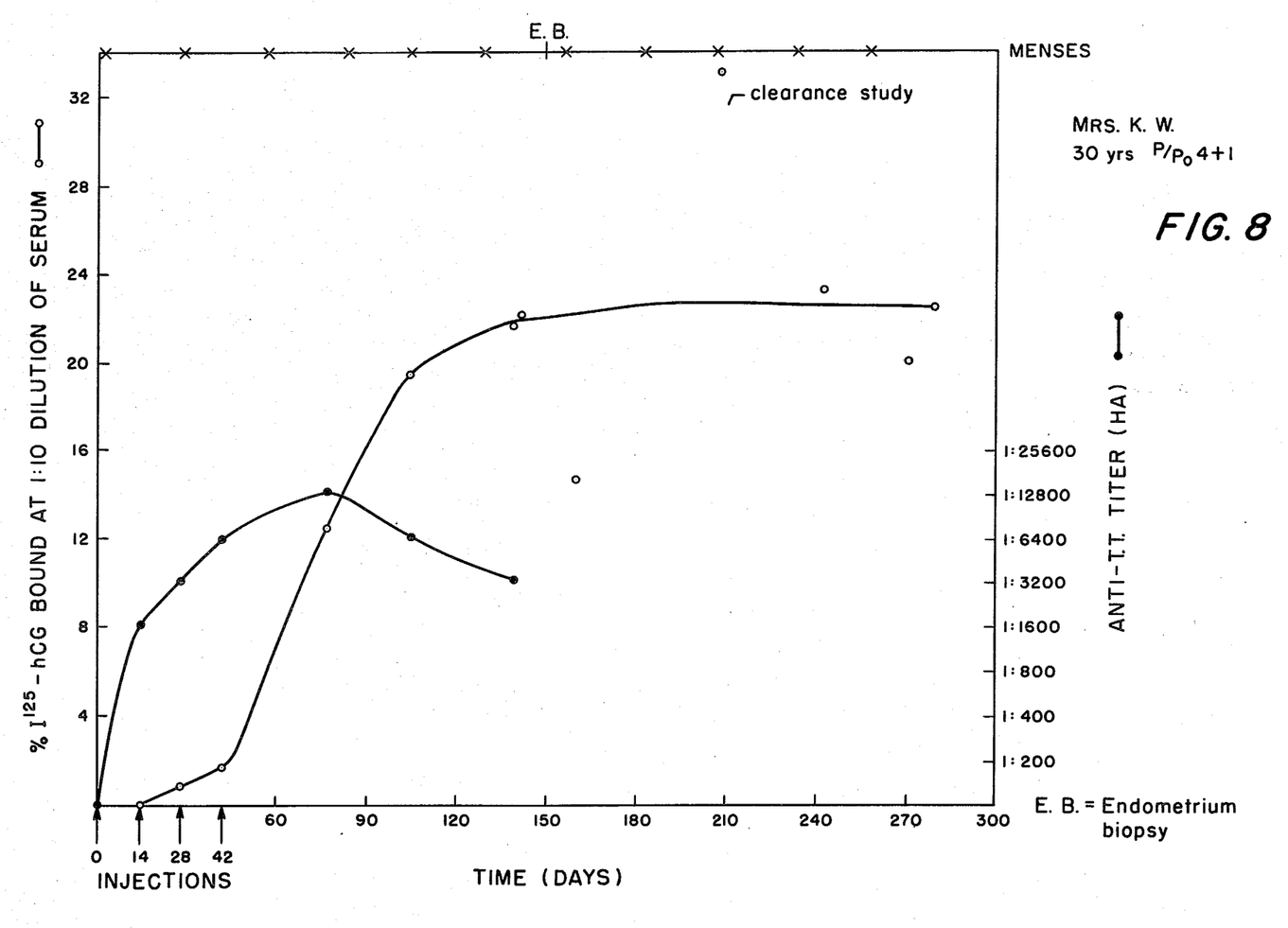

FIGS. 6, 7, and 8 of the attached drawings show the response of the three human volunteers that received the vaccine. Mrs. K. W., FIG. 8 of the drawings, was 30 years old with 5 pregnancies and 4 living children. The rise of antibodies reacting against hCG is shown by the (●——●) curve, and the anti tetanus antibody by the (●——●) curve. The anti hCG titres attained a plateau and have remained at this level at about 9 months after injection. The tests are continuing. The date of menses are indicated by an X mark at the top of the graph. The subject has been menstruating regularly. The endometrium biopsy which was taken at 150 days, showed evidence of ovulation, which was confirmed by vaginal cytology and by the progesterone levels in the secretory phase of the cycle.

The second subject Mrs. A. M., FIG. 7, was 32 years old, with 3 pregnancies and 2 live children. FIG. 7 shows a similar type of immune response kinetics for Mrs. A. M. The endometrium biopsy in her case, as also the vaginal cytology and progesterone levels, indicate the patency of ovulation.

The third subject, Mrs. N. D. (FIG. 6) was 30 years old with 5 pregnancies and 3 live children. Mrs. N. D. had been feeding a child during the firt about 150 days of the study, which explains the lack of menses during this period. Immunization with the vaccine preparation did not produce any disturbance in lactation in spite of a fairly good immune response. She has since started menstruating and has normal menstrual periods.

Libido and other reproductive functions in all 3 subjects have been completely normal. Thorough clinical examination has shown no detectable abnormality of any type. Other parameters such as hematology, (hemoglobin, TLC/DLC, PCV, peripheral smear examination for platelets, reticulocytes), hepatic functions (serum bilirubin, alkaline phosphatase, the transaminases GOT and GPT, LDH isoenzymes, cholinesterase), Renal function tests, blood glucose, serum lipids, cholesterol, triglyceides, free fatty acids, and thyroid function tests were normal and immunization has produced no alteration in organ functions and metabolism. The subjects have also shown normal response to insulin hypoglycaemic test in terms of production of cortisol and growth hormone.

The sera of these immunized women as well as of monkeys and goats hyperimmunized with the B-hCG-TT preparation has been examined by various tests to exclude possible autoimmune reactions against body organs. They were found negative for antinuclear antibodies, antimicrosomal antibodies and were devoid of rheumatoid factor reactivity. This information is summarized below in Table 2.

TABLE 2

| Immunopathology Investigations on Immunized Subjects | | | |
|---|---|---|---|
| Sera from | | Investigations | Observations |
| 1. | N.D. 30 FIG. 6 23.8.74 | 1. Antinuclear antibodies. | No reaction detectable |
| 2. | N.D. 30 20.9.74 | 2. Antimicrosomal antibodies. | the sera tested. |
| 3. | N.D. 30 2.12.74 | 3. Latex agglutination for Rheumatoid factor. | |
| 4. | A.M., 32 FIG. 7 11.10.74 | | |
| 5. | K.W., 30 FIG. 8 28.10.74 | | |
| 6. | K.W., 30 2.12.74 | | |
| 7. | Non-immunized control | | |

They were also found to be negative in their reactivity against human thyroid, parathyroid, adrenals, kidney, testes, and ovaries. The data establishing these facts are summarized in Table 3 below.

TABLE 3

| Reactivity of Anti β-TT sera against Human Organs | | |
|---|---|---|
| Sera from | Human Organs Tested | Observations |
| Normal human female | Thyroid | No reaction of any sera seen by immunofluorescence with any of the organs |
| Immunized human (N.D.) FIG. 6 | Parathyroid | |
| | Adrenal | |
| Normal monkey | Kidney | |
| Immunized monkey | Testis | |

TABLE 3-continued

| Reactivity of Anti β-TT sera against Human Organs | | |
|---|---|---|
| Sera from | Human Organs Tested | Observations |
| | Ovary | |

They were also negative in their reactivity against tissue substrates from mice, rabbit and baboon as summarized in Table 4.

TABLE 4

| Reactivity of Anti β-HCG-TT sera with Tissue substrates from various species | | | |
|---|---|---|---|
| Sera tested | Tissue substrates from | Tests performed | Observations |
| Normal human | Mice | a) Indirect Immunoreacting fluorescence | 1) No tissue antibodies detected |
| Immunized female (N.D.) FIG. 6 Normal monkey Immunized monkey | Rabbit Baboon | b) Anti DNA antibodies | 2) No anti DNA antibodies found |

Figure 9:
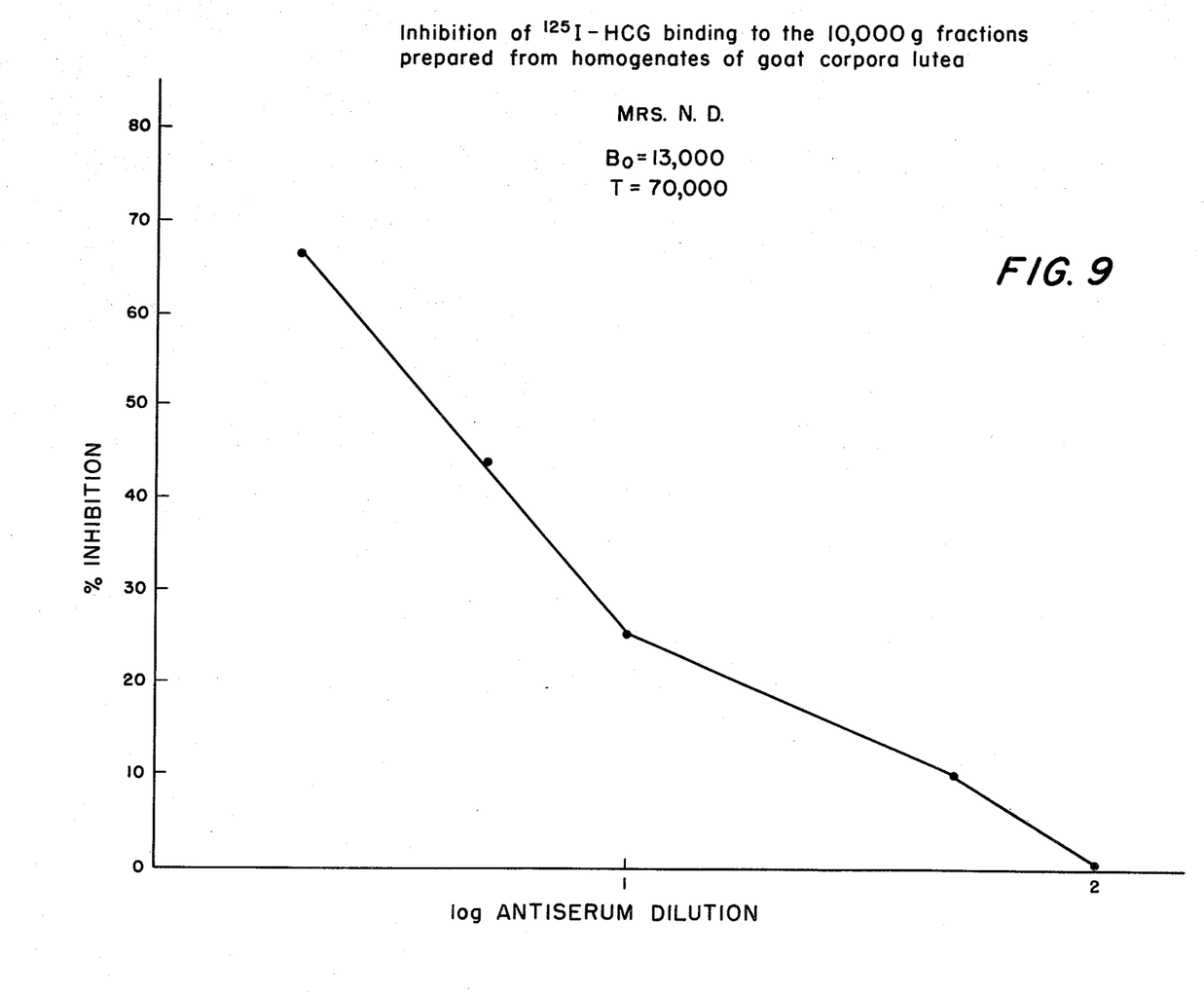
Figure 10:
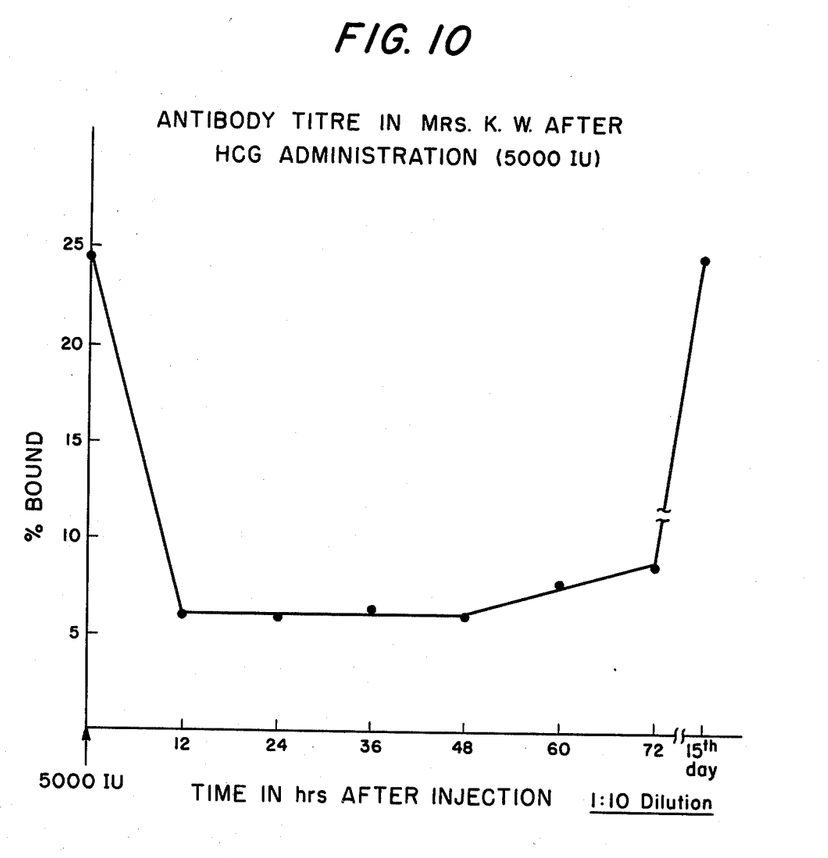

The antibodies generated in the human volunteers were found competent for neutralizing the biological activity of the whole hCG. FIG. 9 of the attached drawings shows the ability of these antibodies from volunteer Mrs. N. D. to block binding of hCG to corpus luteum preparations in a radioreceptors assay. The ability of these antibodies to bind with hCG in vivo is demonstrated by the determinations reported in FIG. 10 of the attached drawings.

The total duration of immune response to hCG in humans following primary immunization with four fortnightly injections of the vaccine is expected to be beyond one year, although individual variations may occur. Active immunization has not evoked undesirable reactions. The subjects have had normal menstrual cycles. There is evidence of ovulation. The kidney, liver, pituitary, cardiovascular, thyroid and other organ functions are normal and undisturbed.

EXAMPLE II

A vaccine was prepared using the Beta-hCG end fragment (BEF) containing the last 32–33 amino acid residues, in place of the immunologically purified beta-hCG used in and following the procedure outlined in Example I. In this Example, beta-hCG end fragment (BEF) comprising the last 32–33 amino acid residues, is covalently linked to tetanus toxoid in a ratio of 40:1 using 1-ethyl-3-(3-dimethyl aminopropyl) carbodiimide. The BEF is obtained from beta-hCG by papain cleavage, as described according to the method described above. Alternatively, the BEF may be synthesized chemically, according to known procedures.

Sufficient vaccine for 30 doses is prepared by mixing 2.5 mg BEF with 300 Lf of tetanus toxoid and 15 mg of 1-ethyl-3-(3-dimethyl aminopropyl) carbodiimide, in phosphate buffer saline pH 7.2 to final volume 5.0 ml. This is incubated at 4° C. for 6 hours with occasional mixing. The product is dialyzed against PBS 7.2 in the cold for 48 hours with 5–6 changes of 1 liter buffer each.

The balance of the procedure, including sterilization and preparation of the vaccine, is the same as described in Example I.

EXAMPLE III

A vaccine was prepared using a nitro derivative of the beta sub-unit of hCG, following the procedure outlined in Example I, $D_1$. The molecular ratio of the derivative to tetanus toxoid was 10:1. The balance of the procedure, including sterilization and preparation of the vaccine, is the same as described in Example I.

I claim:

1. A process for preparing a vaccine for the prevention of pregnancy which comprises:
   (a) obtaining chemically pure beta subunit of human chorionic gonadotropin;
   (b) reacting said chemically pure beta subunit of human chorionic gonadotropin with rabbit antiovine leuteinizing hormone immunosorbent to obtain a beta subunit of human chorionic gonadotropin preparation which is free of determinants capable of reacting with high affinity with anti leuteinizing hormone sera; and
   (c) condensing the thus treated beta subunit of human chorionic gonadotropin preparation with a subject-compatible immunogenic carrier to obtain a vaccine.

2. The process of claim 1 wherein the carrier is tetanus toxoid.

3. The process of claim 1 wherein the immunosorbent is prepared by
   (a) thoroughly dialyzing rabbit antiovine leuteinizing hormone sera against 100 mM phosphate buffered saline at pH 7.2,
   (b) polymerizing the antisera by standing at room temperature for 3 hours with the addition of glutaraldehyde,
   (c) homogenizing the polymerized material followed by washing with phosphatide buffered saline until the washings are free of non-polymerized free protein,
   (d) washing the homogenate with a 200 mM glycine - HCl buffer at pH 2.2,
   (e) neutralizing the homogenate with $K_2HPO_4$ solution, and
   (f) equilibrating the immunosorbent thus produced with phosphatide buffered saline.

4. The process of claim 1 wherein the treated beta subunit of human chorionic gonadotropin is condensed with tetanus toxoid in molecular proportions of 5:1 to 20:1 in the presence of a condensing agent and the resulting product is subjected to the steps of dialyzation and precipitation on alum to form a vaccine.

5. The process of claim 4 wherein the condensing agent is selected from the group consisting of glutaraldehyde and a carbodiimide.

6. The process of claim 4 wherein the condensing agent is 1-ethyl-3-(3-aminopropyl) carbodiimide and the condensing step is conducted at a temperature not in excess of room temperature and for a period not exceeding about 6 hours.

7. The procedss of claim 6 wherein the temperature does not exceed 10° C.

8. The process of claim 5 wherein the condensing agent is glutaraldehyde and the reaction is conducted at a temperature not exceeding 37° C. for a period not exceeding 6 hours.

9. The process of claim 8 wherein the reaction temperature is within the range of about 20°-30° C.

* * * * *

UNITED STATES PATENT AND TRADEMARK OFFICE
CERTIFICATE OF CORRECTION

PATENT NO. : Patent No. 4,161,519
DATED : July 17, 1979
INVENTOR(S) : Gursaran P. Talwar It is certified that error appears in the above-identified patent and that said Letters Patent are hereby corrected as shown below:

Column 4, Line 4, "such a" should read --such as--;

Column 5, Line 12, after "et al." insert an asterisk ( * );

Column 7, TABLE I, heading on third column, "(1-5000)" should read --(1:5000)--;

Column 7, TABLE I, eighth item in last column, "-ng" should simply be -- - --;

Column 7, TABLE I, delete the ninth item in each of the second to seventh columns;

Column 7, Line 50, "P." should read --$P_4$--;

Column 8, Line 56, "●——●" should be --o——o--;

Column 9, Line 6, "firt" should read --first--;

Column 9, Line 11, after "has" insert --had--;

UNITED STATES PATENT AND TRADEMARK OFFICE
CERTIFICATE OF CORRECTION

PATENT NO. : Patent No. 4,161,519
DATED : July 17, 1979
INVENTOR(S) : Gursaran P. Talwar It is certified that error appears in the above-identified patent and that said Letters Patent are hereby corrected as shown below:

Column 9, TABLE 2, in the third column, following the second line (reading "detectable"), insert --with any of--;

Column 10, TABLE 4, first line of main heading, "HCG" should read --hCG--;

Column 10, TABLE 4, the word "reacting" should be removed from the third column and moved to the fourth column (to appear below "1) No tissue"); and Column 12, Line 28, "procedss" should read --process--.

Signed and Sealed this

First Day of January 1980

[SEAL]

Attest:

Attesting Officer

SIDNEY A. DIAMOND
Commissioner of Patents and Trademarks